United States Patent [19]

Kaup

[11] 4,329,882
[45] May 18, 1982

[54] UTILITY POLE INSPECTION KIT

[76] Inventor: Edgar L. Kaup, 2200 S. Raritan St., Englewood, Colo. 80110

[21] Appl. No.: 123,514

[22] Filed: Feb. 22, 1980

[51] Int. Cl.³ ............................................. G01N 1/08
[52] U.S. Cl. .............................................. 73/864.44
[58] Field of Search ................... 73/425, 425.2, 425.4; 408/204

[56] References Cited

U.S. PATENT DOCUMENTS 2,141,261 12/1938 Clark .............................. 73/421.5 R
3,343,421 9/1967 Miller ............................. 73/421.5 R

FOREIGN PATENT DOCUMENTS 173457 11/1960 Sweden ............................... 73/425

OTHER PUBLICATIONS

Devices for Sampling Undisturbed Soil—Engineering News Record, Jul. 20, 1939, vol. 123, pp. 58–60.

*Primary Examiner*—S. Clement Swisher

[57] ABSTRACT

A kit of tools and devices for testing the soundness of underground wooden bodies, such as utility line poles, is provided for effecting the testing of such bodies without removing the ground about the bodies. A straight access tube and a drive rod are provided, the rod having a shoulder for engagement with one end of the tube while a conical end piece on the other end of the rod facilitates driving of the tube through the ground and partially into the wooden body. The access tube is driven into the ground by pounding on the head of the rod, and the rod is withdrawn after the end piece has penetrated the wood and the tube has been set in the body. The kit includes drilling tools for insertion through the tube and the taking of samples of the wood. After sampling, the hole in the wood is treated with a suitable chemical fluid supplied through a tube inserted in the access tube to treat and preserve the wood. On completion of the test and treatment procedure, the hole is closed by inserting a plug through the access tube and tapping it into the hole, whereupon the tube is withdrawn leaving the ground undisturbed.

13 Claims, 17 Drawing Figures

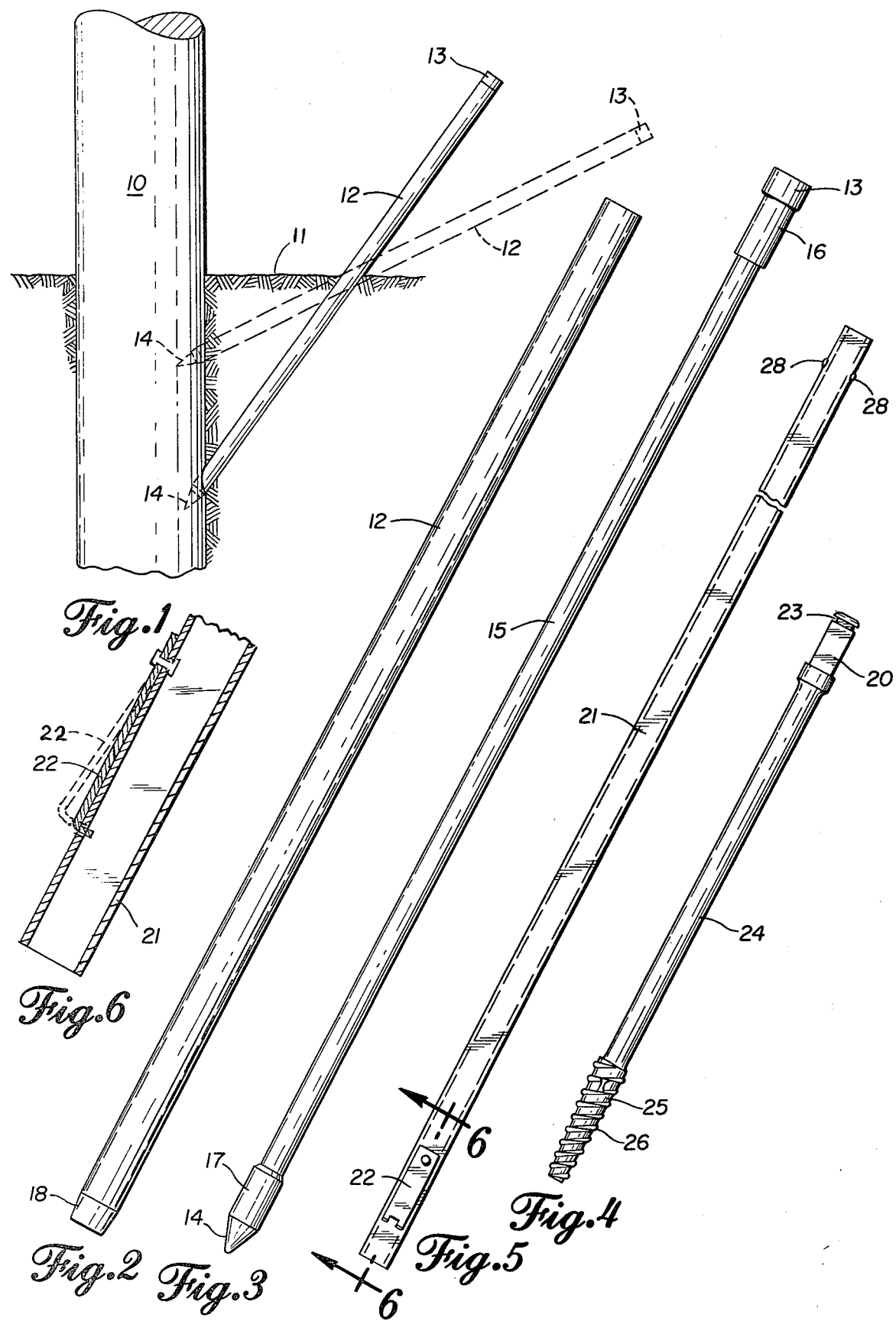

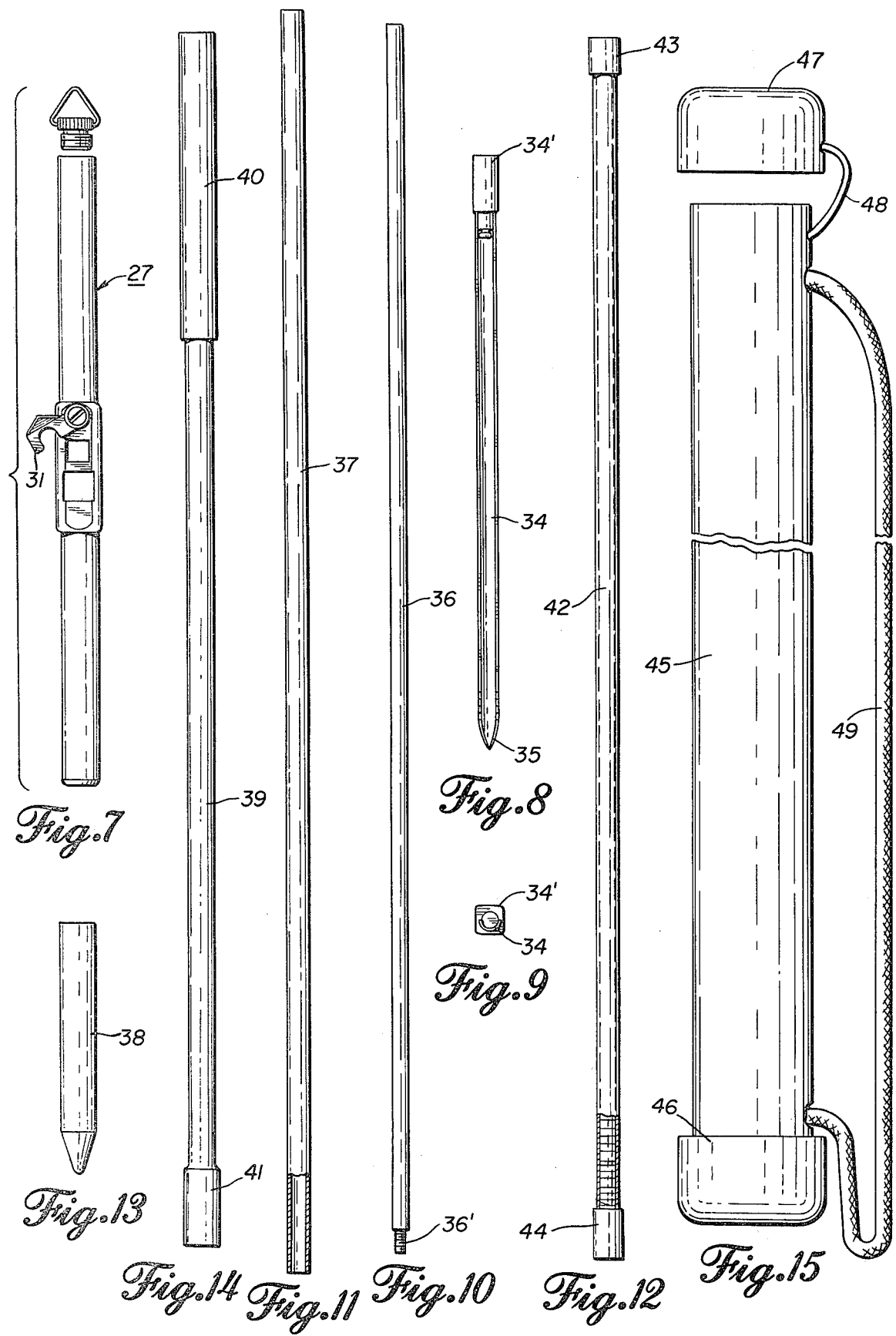

UTILITY POLE INSPECTION KIT

This invention relates to the inspection of wooden bodies lying beneath the surface of the ground, such as the buried lower ends of wooden poles installed on utility lines and particularly to an improved kit for facilitating the inspection of the condition of such bodies below the surface of the ground.

BACKGROUND OF THE INVENTION

Wooden utility poles such as those used for supporting power distribution lines, telephone cables and the like are subject to deterioration below ground due to insects such as carpenter ants and termites and to rotting caused by fungi and bacteria. Such poles are commonly treated by suitable chemicals to preserve the wood and extend the useful life of the buried portions of the pole. This treatment lasts for a substantial time, but eventually its effectiveness decreases to the extent that the pole will be attacked and damaged. In the event of extensive damage the pole must be replaced. Poles are inspected by digging the earth away and sampling the condition of the wood by use of wood auger or a core type drill; if a pole has been damaged but is still suitable for use, chemicals are applied to the pole to treat the damaged areas and to preserve the wood in its usable condition for a further period of time. This process of inspection and treatment is time consuming and costly. Accordingly it is an object of this invention to provide improved apparatus for facilitating the inspection of the underground portions of wooden bodies including wooden utility poles.

It is another object of this invention to provide a kit for facilitating the inspection of wood bodies below ground including an improved device for inspecting the body without disturbing the surrounding earth.

SUMMARY OF THE INVENTION

Briefly, in carrying out the objects of this invention in one embodiment thereof, a testing kit is provided which includes a device for providing access to the underground zone of a utility line pole or other wooden body to be tested without requiring the removal of ground about the body, and drilling and sample removal devices cooperating with the access device to facilitate the testing of the wooden body and further devices for facilitating the treatment of the pole with fluids and thereafter plugging the test hole. The access device comprises a tube of selected length and a driving rod having a pointed head positioned to project from the far end of the tube when a shoulder at the other end of the rod engages the near end of the tube. The tube and head are driven downwardly at an inclination to the pole or other body until the head and a portion of the tube enter the body whereupon the rod is removed leaving the tube in position at a centered locating hole ready for the sampling bit to enter the tube and be drilled into the body to produce the sample. If the bit is of the core producing type a sample retrieving member is moved into position to remove the core; if the bit is an auger its removal will more the sample out of the tube with it when withdrawn so that the sample can be retrieved. The kit of this invention is usable for testing the condition of various underground wooden bodies, and, for example, may be used for testing the condition of tree roots without disturbing the ground around the root.

The features of novelty which characterize the invention are pointed out with particularity in the claims annexed to and forming a part of this specification. The invention itself, however, together with further objects and advantages thereof, will best be understood from the detailed description below taken in connection with the accompanying drawings.

BRIEF DESCRIPTION OF THE DRAWINGS

FIG. 1 is an elevation view, partly in section, of a utility pole with an access tube embodying the invention shown in position;

FIG. 2 is an enlarged view of the access tube of FIG. 1;

FIG. 3 is an enlarged view of the tube driving member of FIG. 1;

FIG. 4 is an enlarged side elevation of a coring bit for use with the tube of FIG. 1;

FIG. 5 is a side elevation of a driving rod for the bit of FIG. 4;

FIG. 6 is an enlarged sectional view taken along the line 6—6 of FIG. 5;

FIG. 7 is a top plan view of a handle for rotating the rod of FIG. 5;

FIG. 8 is an enlarged view of a sample extracting tang for use within the bore of the bit of FIG. 4;

FIG. 9 is a bottom end view of the tang of FIG. 8;

FIG. 10 is a longitudinal elevation view of a manipulating shaft for the tank of FIG. 8;

FIG. 11 is a longitudinal view of a treating fluid injection tube;

FIG. 12 is a longitudinal view of a clear plastic storing tube for samples;

FIG. 13 is a longitudinal view of a round plug for a hole drilled by the bit of FIG. 4;

FIG. 14 is a longitudinal view of a tamping rod for driving the plug of FIG. 13;

FIG. 15 is a longitudinal elevation view of a container of the components of the kit shown in FIGS. 2 through 14;

DESCRIPTION OF PREFERRED EMBODIMENT

Figure 16:
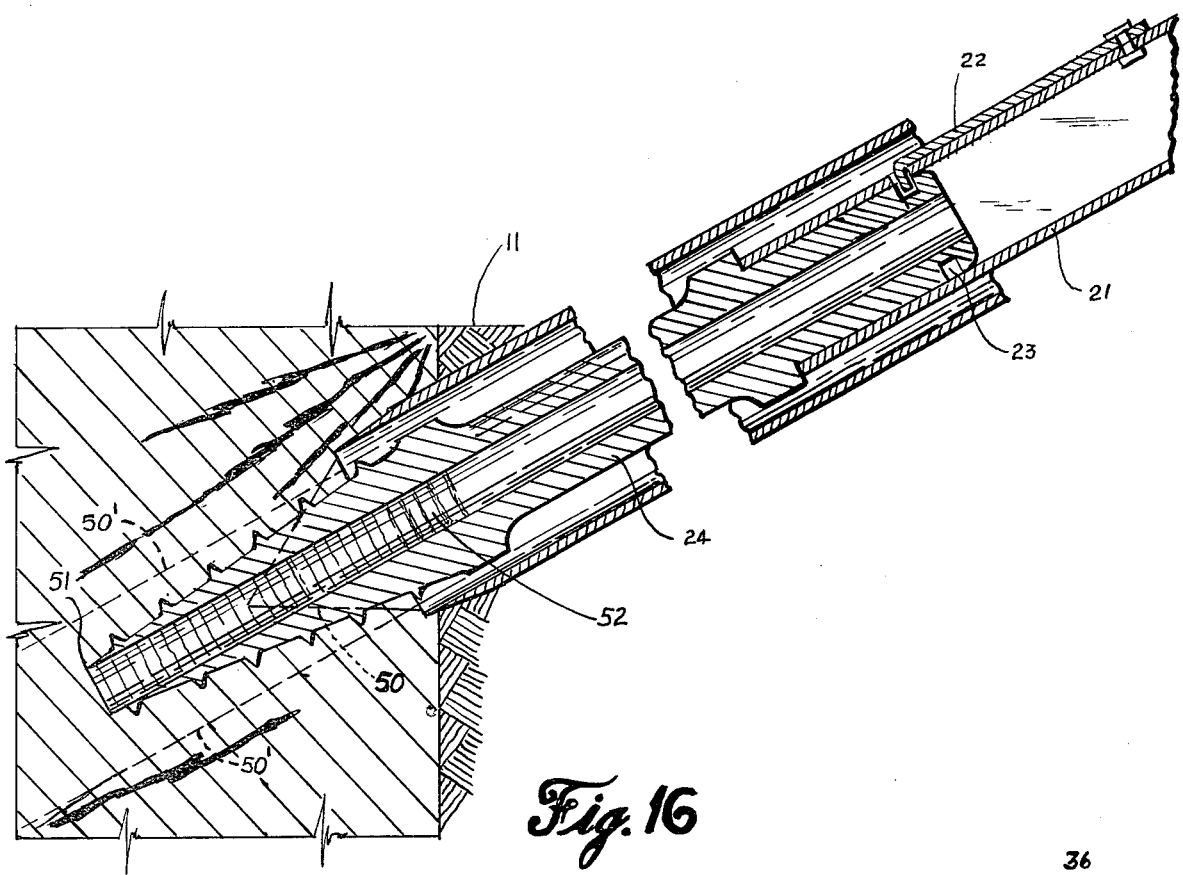
FIG. 16 is an enlarged view partly broken away of the lower end of the tube assembly in position in a pole shown in FIG. 1.

Referring now to the drawing, FIG. 1 illustrates a wooden utility pole 10 set in place and extending well below the ground 11 in which it is secured. An access tube 12 is shown in position, inclined downwardly and having its lower end driven a short distance into the pole. The tube 12 has been driven into place by a driving rod having a striking head 13 and a pointed penetration head 14 extending beyond the lower end of the tube. The head has been shown as having been driven into the pole sufficiently far that the tube 10 has entered the wood of the pole. The angle at which the tube is driven is determined by the operator for purposes of reaching the desired test location. An alternative position of the tube is shown in the dotted lines. After the tube has been set, the drive rod is withdrawn leaving the tube end seated in the pole adjacent the cavity formed by the head 14.

The configuration of the tube 10 is shown in FIG. 2 and that of the driving rod is shown in FIG. 3. The driving rod includes a shaft 15 having the striking head 13 at its upper end and the penetration head 14 at its lower end. The driving head includes an extension 16 which fits within the end of the tube and holds the head 13 centered in the tube so that the head rests on the tube on the shoulder formed between the head and extension. The end of the tube 12 lies transversely to the tube axis and has been illustrated as flat and normal to the axis so that the head engages it in flat face contact on all sides. When the head is struck by a hammer it drives the tube with it. Other configurations of the transverse end faces of the tube may, however, be employed, if desired, provided that the required driving relationship is obtained. The penetration head 14 includes an extension 17 which fits closely within the tube and centers the driving point. The outside of the lower end of the tube 12 is beveled or sloped, as shown at 18, to conform to the slope of the point and form a continuous penetrating surface which facilitates the driving of the tube into the pole.

After the rod 15 has been withdrawn a sample of the wood in alignment with the tube is taken by a suitable bit illustrated in FIG. 4 as a coring bit. The bit includes an attaching shank 20 of square cross section which fits in the end of a square tubular driving rod 21 and is secured by a spring clip 22, shown enlarged in FIG. 6, having an inwardly extending end 22' which passes through the wall of the rod 21 into engagement with a groove 23 in the shank 20. The cross section of the square tubular rod 21 is of a size to fit loosely within the tube 12, the diagonal of the square section being somewhat less than the inside diameter of the tube; thus the corners of the rod 21 afford easy sliding of the rod within the tube and also hold the rod substantially centered in the tube. The cone shaped hole formed by the penetration head 14 also facilitates the centering of the bit for drilling. The bit comprises a hollow shaft 24 and a tapered or cone shaped cutting head 25 which terminates in a sharp annular edge at its end for cutting the core. The head 25 is provided with a helical cutting thread 26 which draws the head into the wood and cuts a bore hole. The core cut by the sharp front edge of the bit enters and is retained in the hollow shaft 24.

A handle 27, shown in FIG. 7, is used to turn the bit. The handle is hollow and the bit may be stored within the handle. The handle has a square hole near its center which fits the square rod 21 and the handle rests against stops 28 formed on the four corners of the rod. The handle is also provided with a smaller square hole 30 which fits the square shank 20 of the bit, and the bit when used alone with the handle is locked in place in the hole 30 by a swingable catch 31 which engages the groove 23 of the shank. The handle has a threaded closure 32 for retaining the bit within the handle, and the closure is provided with a bail 33 so that the handle may be hung on a nail or peg or be attached to a workman's belt.

When the desired length of core has been cut it is removed by inserting tang 34, shown in FIG. 8, into the bit. The tang, which has a channel shaped cross section as shown in FIG. 9, is inserted with its channel facing down, its sharp edged pointed end passes down along the core and teeth 35 engage the core. The tang is secured to a rod 36, shown in FIG. 10, by a threaded fitting or connection 36' and is manipulated by the rod which passes through the hollow driving rod 21. When the tang is in place with its attaching head 34' threaded tightly on the connector 36' the rod 36 is turned one-half turn so that the channel faces upwardly, whereupon the core may be withdrawn intact on the tang as the rod 36 is removed.

After the core has been withdrawn the rod 21 and bit 24 are removed and the hole 50' may then be filled with any suitable insecticide or other treating fluid, either liquid or gaseous, by utilizing a straight tube 37 shown in FIG. 11. The tube 37 is inserted through the tube 12 until it is in or near the hole drilled by the bit 24 and the treating fluid is then supplied to the top of the tube from the nozzle of a squeeze bottle commonly employed for distributing liquid chemicals or from a gas cylinder. After the treating fluid has been discharged into the hole, a wooden plug 38 shown in FIG. 13 is moved down the tube 12 and into the hole by a tamping rod 39 having a handle 40 and a tamping head 41. The plug 38 is tamped securely in place whereupon the tamping rod and the tube 12 are removed leaving the ground undisturbed about the foot of the pole.

The core after its removal on the tang 34 may be placed intact in a transparent plastic storage tube 42 shown in FIG. 12. The tube 12 is provided with detachable end caps 43 and 44.

All of the components illustrated in FIG. 1 through FIG. 14 are arranged to be carried in a cylindrical case 45, shown in FIG. 15, and which has a bottom closure 46 secured rigidly thereto and a top detachable cap 47. The cap is secured to the cylinder 45 by a suitable wire or cable 48 and the cylinder 45 is provided with a carrying rope 49. The handle 27, as indicated above, is arranged to hold the bit 24 and the tang 34 which are stored inside the handle. In the carrying case 45 the rod 15 is carried within the tube 12 and many components are fitted within the case in which they are readily carried about by the testing crew and are ready for use at any time. The illustrated arrangement of the tube 12 and the driving rod 15 provides a simple and effective mechanism for providing a rigid access passage to the selected portion of the wooden pole below ground so that the tube 12 is securely held during the testing procedure and the treatment and plugging of the hole are performed for completiion of the testing routine.

Figure 17:
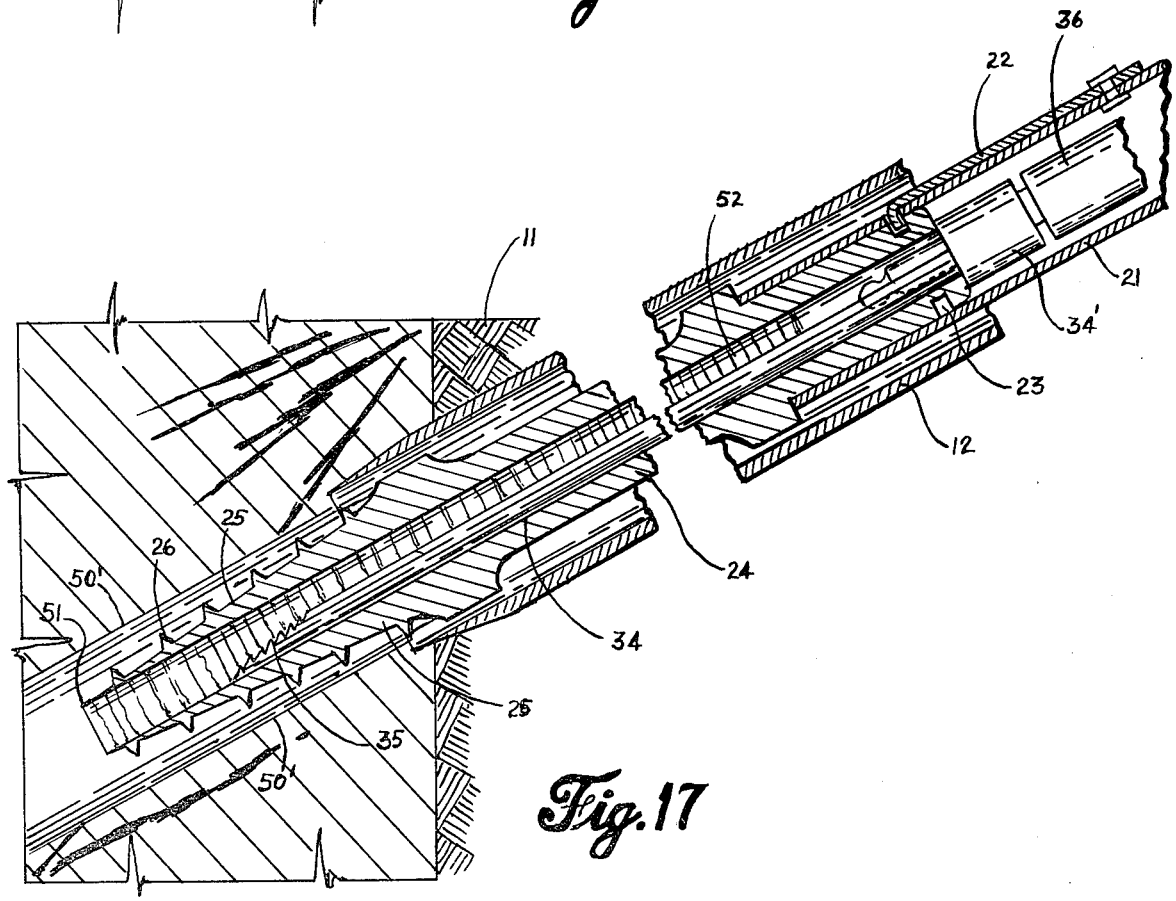
FIG. 17 is a view similar to FIG. 16 showing the bit after drilling and withdrawn to a position near to the outlet of the bore.

The manner in which the foregoing procedure is effected will be understood more fully from FIG. 16 which is an enlarged view in section of the tube 12 and the coring bit shown in position just after the start of the boring of the bit into the pole for taking a core. Here the lower end of the tube 12 has been illustrated as having entered and being held in the wood of the pole and the bit is in position for further drilling beyond the original cavity, indicated at 50, which has been formed by driving the pointed end of the rod 15 into the pole. The cutting head 25 is illustrated as having been driven a short distance beyond the original conical hole 50 so that the sharp annular front edge 51 has cut a short length of core 52. As the bit is turned it will proceed downwardly along the sloping line into the pole and the core will continue to be formed and will be carried in the center passage or bore of the cutting head. The hole to be formed by the drillhead 25 is indicated by parallel dotted lines 50'. This hole is formed by cutting the core which moves into the hollow bit and by compressing the rest of the wood outwardly by the wedging action of the bit. When the hole has been driven to the desired depth, the core is removed by inserting and using the tang 34. It will be understood that in the final position of the bit when the hole has been drilled and the core is in the bore of the bit, the cutting head 25 will be at the bottom of the completed hole. The connecting head of the tang indicated at 34' has been shown in FIG. 17 as connected to the rod 36 by which the tang is manipulated. When the core 52 is to be extracted the tang 34 is inserted in the bore of the bit in this position with its channel facing down and is then rotated one-half revolution until the channel thereof faces upwardly as shown in FIG. 17. This twisting operation breaks the core from the lower end and the core may then be removed by withdrawing the rod 36 and tang 34 with the core lying in the channel or, if desired, the drill may be removed with the tang and core in place as shown in FIG. 17 in which the drill head 25 is shown as having been moved outwardly to the entrance of the completed hole 50 with the core in place in the tang channel; the tang may then be removed or it may be removed when the bit is outside the tube 10.

From the foregoing it will be seen that this invention provides at readily portable and easily used kit of cooperating tools for efficiently effecting the testing of wooden utility poles and the like below ground and without the necessity of digging away the ground for purposes of access and inspection.

While specific arrangements and features of the invention have been illustrated and described, various modifications and other applications will occur to those skilled in the art. Therefore, it is not desired that the invention be limited to the specific constructions illustrated and described and it is intended by the appended claims to cover all modifications which fall within the spirit and the scope of the invention.

I claim:

1. An inspection kit for testing the condition of a wooden body below the surface of the ground comprising:
    a straight metal tube having a length sufficient to extend from the body at the position to be tested upwardly to a position above the ground, the end faces of the tube lying transversely to its axis,
    a drive rod having a pointed end member closely fitting within the tube and slidable within the tube and extending beyond the lower end thereof, said rod having a shoulder at its upper end adapted to lie in engagement with the upper end face of said tube when said pointed member protrudes from the other end thereof, whereby said tube is adapted to be driven through the earth by blows against said rod into position against the wooden body with said pointed end and a portion of the adjacent end of said tube penetrating the body and said rod is adapted to be withdrawn leaving said tube in position in the ground to receive a boring tool or the like for producing a test sample of the wood of the body in alignment with the tube,
    a core bit of a size to pass through said tube and to extend therebeyond,
    means adapted to be connected with said bit for turning said bit for producing a core of wood from the body, and
    means for withdrawing the core through said tube intact.

2. An inspection kit as set forth in claim 1 wherein the outer surface of the end of the tube adjacent said pointed end is tapered in general alignment with the slope of said pointed end to facilitate the driving of the end of said tube into the wooden body.

3. An inspection kit for testing the condition of a wooden body below the surface of the ground comprising:
    a straight metal tube having a length sufficient to extend from the body at the position to be tested upwardly to a position above the ground, the end faces of the tube lying transversely to its axis,
    a drive rod having a pointed end member closely fitting within the tube and slidable within the tube and extending beyond the lower end thereof, said rod having a shoulder at its upper end adapted to lie in engagement with the upper end face of said tube when said pointed member protrudes from the other end thereof, whereby said tube is adapted to be driven through the earth by blows against said rod into position against the wooden body with said pointed end and a portion of the adjacent end of said tube penetrating the body and said rod is adapted to be withdrawn leaving said tube in position in the ground to receive a boring tool or the like for producing a test sample of the wood of the body in alignment with the tube,
    a tamping rod for insertion within said tube and having a head adapted to engage a filler plug for filling the hole after removal of the sample whereby a treated wooden plug having a diameter to fit the bored hole may be inserted in the tube and thereafter tamped into place with said rod.

4. An inspection kit as set forth in claim 3 wherein the outer surface of the end of the tube adjacent said pointed end is tapered in general alignment with the slope of said pointed end to facilitate the driving of the end of said tube into the wooden body.

5. An inspection kit for testing the condition of a wooden body below the surface of the ground comprising:
    a straight metal tube having a length sufficient to extend from the body at the position to be tested upwardly to a position above the ground, the end faces of the tube lying transverseley to its axis,
    a drive rod having a pointed end member closely fitting within the tube and slidable within the tube and extending beyond the lower end thereof, said rod having a shoulder at its upper end adapted to lie in engagement with the upper face of said tube when said pointed member protrudes from the other end thereof, whereby said tube is adapted to be driven through the earth by blows against said rod into position against the wooden body with said pointed end and a portion of the adjacent end of said tube penetrating the body and said rod is adapted to be withdrawn leaving said tube in position in the ground to receive a boring tool or the like for producing a test sample of the wood of the body in alignment with the tube,
    said means for turning said bit including a shaft adapted to be attached to said bit and rotatably and slidably movable within said tube and of a length to extend from the shank of said bit to a position outside said tube, and a cross handle adapted to be secured to said shaft for turning said shaft and the bit.

6. An inspection kit as set forth in claim 5 wherein the outer surface of the end of the tube adjacent said pointed end is tapered in general alignment with the slope of said pointed end to facilitate the driving of the end of said tube into the wooden body.

7. An inspection kit as set forth in claim 5 or 6 wherein said shaft is of square cross section and said handle has a transverse hole of square cross section for fitting said shaft and for turning said bit, and wherein said bit has a portion of square cross section at its connecting end adapted to be engaged by the inner wall of said shaft to afford positive rotation of said bit by said shaft.

8. An inspection kit as set forth in claim 5 or 6 wherein said handle has a second transverse hole of square cross section for fitting said bit portion whereby said handle is adapted to be used directly with said bit to turn said bit for taking a sample of the wood from an exposed area of a wooden body.

9. An inspection kit as set forth in claim 7 wherein the corners of said square shaft fit in frictional engagement with the inner wall of said tube whereby said shaft is centered in said tube.

10. An inspection kit as set forth in claim 9 wherein said cross handle is tubular and closed at one end and has a removable closure at its other end, said handle being of a size to contain and store said bit.

11. An inspection kit as set forth in claim 10 wherein said bit has a passage for receiving the samples and said shaft is tubular and provides a continuity of said passage in said bit, a trough like sample extracting element adapted to be positioned within the passage of said bit to receive a sample, and means including a rod-like member adapted to pass through said shaft and to engage said element for inserting said element in said bit and for withdrawing said element with a sample thereon for removing the sample.

12. The method for sampling the condition of a wooden body below the surface of the ground which comprises:
providing a straight metal tube long enough to extend through the ground to the wooden body,
providing a rod having a length sufficient to reach through the tube and having a pointed end adapted to extend beyond the tube,
placing a rod in the tube with its end extending from the end of the tube driving the tube and the rod together through the ground and against the body,
removing the rod while leaving the tube with its end in place in the body,
providing a sampling drill and utilizing the indentation made by the point of the rod as a starting hole for the drill and operating the drill for obtaining a sample of the wood of the body, and
withdrawing the sample through the tube.

13. The method set forth in claim 12 wherein the drill is a core drill and including the step of withdrawing the core sample intact.

* * * * *